US009034836B2

(12) United States Patent
Dodge et al.

(10) Patent No.: US 9,034,836 B2
(45) Date of Patent: May 19, 2015

(54) GENE THERAPY FOR AMYOTROPHIC LATERAL SCLEROSIS AND OTHER SPINAL CORD DISORDERS

(75) Inventors: James Dodge, Shrewsbury, MA (US); Lamya Shihabuddin, Brighton, MA (US); Catherine O'riordan, Waban, MA (US)

(73) Assignee: Genzyme Corporation, Cambridge, MA (US)

( * ) Notice: Subject to any disclaimer, the term of this patent is extended or adjusted under 35 U.S.C. 154(b) by 351 days.

(21) Appl. No.: 12/328,267

(22) Filed: Dec. 4, 2008

(65) Prior Publication Data

US 2010/0267812 A1     Oct. 21, 2010

Related U.S. Application Data

(63) Continuation of application No. PCT/US2007/013391, filed on Jun. 7, 2007.

(60) Provisional application No. 60/811,419, filed on Jun. 7, 2006.

(51) Int. Cl.
| A61K 48/00 | (2006.01) |
| A61K 39/23 | (2006.01) |
| C12N 15/00 | (2006.01) |
| C12N 15/63 | (2006.01) |
| C07H 21/04 | (2006.01) |

(52) U.S. Cl.
CPC ............ *A61K 48/0075* (2013.01); *A61K 48/005* (2013.01); *C12N 2799/025* (2013.01)

(58) Field of Classification Search
CPC .............. A61K 48/005; A61K 48/0075; C12N 2799/025
USPC ........... 424/233.1; 435/320.1, 455; 514/44 R; 536/23.5
See application file for complete search history.

(56) References Cited

U.S. PATENT DOCUMENTS

| 6,042,576 A | 3/2000 | DeVries |
| 6,468,524 B1 | 10/2002 | Chiorini et al. |
| 2002/0049178 A1 | 4/2002 | Goldman et al. |
| 2004/0076613 A1* | 4/2004 | Mazarakis et al. |
| 2004/0110707 A1 | 6/2004 | Maden et al. |
| 2005/0032219 A1 | 2/2005 | Aubourg et al. |
| 2005/0084906 A1 | 4/2005 | Goetsch et al. |

FOREIGN PATENT DOCUMENTS

| EP | 0130166 | 1/1985 |
| WO | WO-2006/119341 A2 | 11/2006 |
| WO | WO-2006/119341 A3 | 11/2006 |

OTHER PUBLICATIONS

Gorecki, D., 2001, Expert Opin. Emerging Drugs, 6(2): 187-198.*
Zaiss et al., 2005, Current Gene therapy, vol. 5, pp. 323-331.*
Flotte, T., 2005, Current Gene therapy, vol. 5, pp. 361-366.*
Castro et al., 2001, Histl. Histopathol., vol. 16, p. 1225-1238.*
Lowenstein et al., 2002, Current Opinion in Molecular Therapeutics, vol. 4, No. 4, pp. 359-371.*
Skolnick et al., 2000, Trends in Biotech, vol. 18, pp. 34-39.*
Tomasinsig et al., 2005, Current Protein and Peptide Science, vol. 6, pp. 23-34.*
Smallwood et al., 2002, Virology, vol. pp. 135-145.*
Chattopadhyay et al., 2004, Virus Research, vol. 99, pp. 139-145.*
PCT Int. Search Report.
*HO, et al., Synthetic Protein Transduction Domains: Enhances Transduction Potential in Vitro and in Vivo. cancer Research, Jan. 2001, vol. 61, pp. 474 and 475.
Azzouz, M. et al. (May 27, 2004). "VEGF Delivery With Retrogradely Transported Lentivector Prolongs Survival in a Mouse ALS Model," *Nature* 429:413-417.
De Pagter-Holthuiezen, P. et al. (Jan. 1986). "Organization of the Human Genes for Insulin-Like Growth Factors I and II," *Febs* 195(1,2):179-184.
Kalnins, A. et al. (1983). "Sequence of the *lacZ* Gene of *Escherichia coli*," *The Embo Journal* 2(4):593-597.
Kaspar, B.K. et al. (Aug. 8, 2003). "Retrograde Viral Delivery of IGF-1 Prolongs Surival in a Mouse ALS Model," *Science* 301:839-842.
Liu, G. et al. (Oct. 12, 2005). "Functional Correction of CNS Phenotypes in a Lysosomal Storage Disease Model Using Adeno-Associated Virus Type 4 Vectors," *The Journal of Neuroscience* 25(41):9321-9327.
Tischer, E. et al. (Jun. 25, 1991). "The Human Gene for Vascular Endothelial Growth Factor. Multiple Protein Forms are Encoded Through Alternative Exon Splicing," *The Journal of Biological Chemistry* 256(18):11947-11954.
Tsien, R.Y. et al. (1998. "The Green Fluorescent Protein," *Annu. Rev. Biochem.* 67:509-544.
The Notification of Reexamination for Chinese Patent Application No. 200780020891.5, filed on Dec. 21, 2007, mailed on Apr. 26, 2012, four pages.
European Examination Report mailed on Sep. 13, 2013, for EP Application No. 12152550.5, filed on Jun. 7, 2007, 6 pages,
Guan, J. et al. (Jan. 31, 1996). "The Movement of IGF-I Into the Brain Parenchyma After Hypoxic-Ischaemic Injury," *NeuroReport* 7(2):632-636.
Guan, J. et al. (2000). "Intracerebral Transportation and Cellular Localisation of Insulin-Like Growth Factor-1 Following Central Administration to Rats with Hypoxic-Ischemic Brain Injury," *Brain Research* 853:163-173.

(Continued)

*Primary Examiner* — Shin-Lin Chen
(74) *Attorney, Agent, or Firm* — Morrison & Foerster LLP

(57) ABSTRACT

This disclosure provides methods and compositions for treating disorders or injuries that affect motor function and control in a subject. In one aspect, the invention a transgene product is delivered to a subject's spinal cord by administering a recombinant neurotrophic viral vector containing the transgene to the brain. The viral vector delivers the transgene to a region of the brain which is susceptible to infection by the virus and which expresses the encoded recombinant viral gene product. Also provided are compositions for delivery of a transgene product to a subject's spinal cord by administering a recombinant neurotrophic viral vector containing the transgene to the subject's brain.

9 Claims, 13 Drawing Sheets

(56) References Cited

OTHER PUBLICATIONS

Passini, M.A. et al. (Jun. 2003). "Intraventricular Brain Injection of Adeno-Associated Virus Type I (AAV1) in Neonatal Mice Results in Complementary Patterns of Neuronal Transduction to AAV2 and Total Long-Term Correction of Storage Lesions in the Brains of β-Glucuronidase-Deficient Mice," *Journal of Virology* 77(12):7034-7040.

Skold, M. et al. (2002). "Induction of HIF1alpha in Motoneurons After Intraspinal Axotomy," 32nd Annual Meeting of the Society for Neuroscience, Orlando, Florida, Nov. 2-7, 2002, abstract, one page.

Skold, M. et al. (Jul. 1, 2004). "Induction of HIF1 alpha but not HIF2alpha in Motoneurons After Ventral Funiculus Axotomy—Implication in Neuronal Survival Strategies," *Biosis, Experimental Neurology*, 188:20-32, Abstract 1 page.

Tan, X.-J. et al. (Apr. 18, 2006). "Therapeutic Effect of Hypoxia-Inducible Factor-1 alpha on Focal Cerebral lschemia: Experiment With Rats," *Zhonghua Yi Xue Za Zhi, National Medical Journal of China* 86(15):1057-1060. (Translation of the Abstract Only.).

Tao, T. et al. (Sep. 2005). "Effects of Adenovirus-Mediated HIF-1α Gene Transfer on Cerebral Infarct Volume After Focal Cerebral lschemia in Rats," *Fudan Univ. J. Med. Sci. Xuebao (Yixuekexueban)* 32(5):594-596. (English Translation of Chinese Abstract Only.).

\* cited by examiner

GENE THERAPY FOR AMYOTROPHIC LATERAL SCLEROSIS AND OTHER SPINAL CORD DISORDERS

FIELD OF THE INVENTION

The present invention relates to compositions and methods for treating disorders affecting a subject's motor function and in particular, motor function affected by disease or injury to the brain and/or spinal cord.

Gene therapy is an emerging treatment modality for disorders affecting the central nervous system (CNS). CNS gene therapy has been facilitated by the development of viral vectors capable of effectively infecting post-mitotic neurons. The central nervous system is made up of the spinal cord and the brain. The spinal cord conducts sensory information from the peripheral nervous system to the brain and conducts motor information from the brain to various effectors. For a review of viral vectors for gene delivery to the central nervous system, see Davidson et al. (2003) Nature Rev. 4:353-364.

Adeno-associated virus (AAV) vectors are considered useful for CNS gene therapy because they have a favorable toxicity and immunogenicity profile, are able to transduce neuronal cells, and are able to mediate long-term expression in the CNS (Kaplitt et al. (1994) Nat. Genet. 8:148-154; Bartlett et al. (1998) Hum. Gene Ther. 9:1181-1186; and Passini et al. (2002) J. Neurosci. 22:6437-6446).

One useful property of AAV vectors lies in the ability of some AAV vectors to undergo retrograde and/or anterograde transport in neuronal cells. Neurons in one brain region are interconnected by axons to distal brain regions thereby providing a transport system for vector delivery. For example, an AAV vector may be administered at or near the axon terminals of neurons. The neurons internalize the AAV vector and transport it in a retrograde manner along the axon to the cell body. Similar properties of adenovirus, HSV, and pseudorabies virus have been shown to deliver genes to distal structures within the brain (Soudas et al. (2001) FASEB J. 15:2283-2285; Breakefield et al. (1991) New Biol. 3:203-218; and deFalco et al. (2001) Science, 291:2608-2613).

Several groups have reported that the transduction of the brain by AAV serotype 2 (AAV2) is limited to the intracranial injection site (Kaplitt et al. (1994) Nat. Genet. 8:148-154; Passini et al. (2002) J. Neurosci. 22:6437-6446; and Chamberlin et al. (1998) Brain Res. 793:169-175). Recent reports suggest that retrograde axonal transport of neurotrophic viral vectors can also occur in select circuits of the normal rat brain (Kaspar et al. (2002) Mol. Ther. 5:50-56 (AAV vector); Kasper et al. (2003) Science 301:839-842 (lentiviral vector) and Azzouz et al. (2004) Nature 429:413-417 (lentiviral vector). Roaul et al. (2005) Nat. Med. 11(4):423-428 and Ralph et al. (2005) Nat. Med. 11(4):429-433 report that intramuscular injection of lentivirus expressing silencing human Cu/Zn supreoxide dismutase (SOD1) interfering RNA retarded disease onset of amyotrophic lateral sclerosis (ALS) in a therapeutically relevant rodent model of ALS.

Cells transduced by AAV vectors may express a therapeutic transgene product, such as an enzyme or a neurotrophic factor, to mediate beneficial effects intracellularly. These cells may also secrete the therapeutic transgene product, which may be subsequently taken up by distal cells where it may mediate its beneficial effects. This process has been described as cross-correction (Neufeld et al. (1970) Science 169:141-146).

However, a need still exists for compositions and methods to treat dysfunction of the spinal cord that result in loss of motor function in human patients. This invention satisfies this need and provides related advantages as well.

SUMMARY OF THE INVENTION

This invention provides methods and compositions to deliver a transgene to the spinal cord and/or the brainstem region of a subject by intraventricular administration of a recombinant neurotrophic viral vector containing an IGF-1 transgene. The viral delivery may be under conditions that favor expression of the transgene in ependymal cells.

This invention provides methods and compositions to deliver a transgene to the spinal cord and/or the brainstem region of a subject by intraventricular administration of a recombinant neurotrophic viral vector comprising a transgene selected from the group consisting of insulin growth factor-1 (IGF-1), calbindin D28K, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen. The viral delivery may be under conditions that favor expression of the transgene in ependymal cells.

This invention provides methods and compositions to deliver a transgene to the spinal cord and/or the'brainstem region of a subject by intraventricular (known also as intracerebroventricular or ICV) administration of a recombinant neurotrophic viral vector comprising at least two transgenes selected from the group consisting of insulin growth factor-1 (IGF-1), calbindin D28K, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen. In one embodiment, a recombinant adeno-associated viral vector comprises IGF-1 and VEGF. The viral delivery may be under conditions that favor expression of the transgene in ependymal cells. Tables 1-3 provide potential combinations of transgene pairs useful in the instant invention.

In a further aspect, the invention provides compositions and method to ameliorate the symptoms of a motor neuron disorder in a subject by administering a recombinant neurotrophic viral vector containing the therapeutic transgene to the subject's brain and under conditions that favor expression of the transgene in a therapeutically effective amount.

It is to be understood that both the foregoing general description and the following detailed description are exemplary and explanatory only and are not restrictive of the invention as claimed.

BRIEF DESCRIPTION OF THE FIGURES

FIG. 13 also shows a comparison of hindlimb strength between SOD mice that received intraventricular administration of AAV4 encoding GFP versus AAV4 encoding VEGF165. VEGF165 recipients lost strength more gradually and later.

Figure 1:
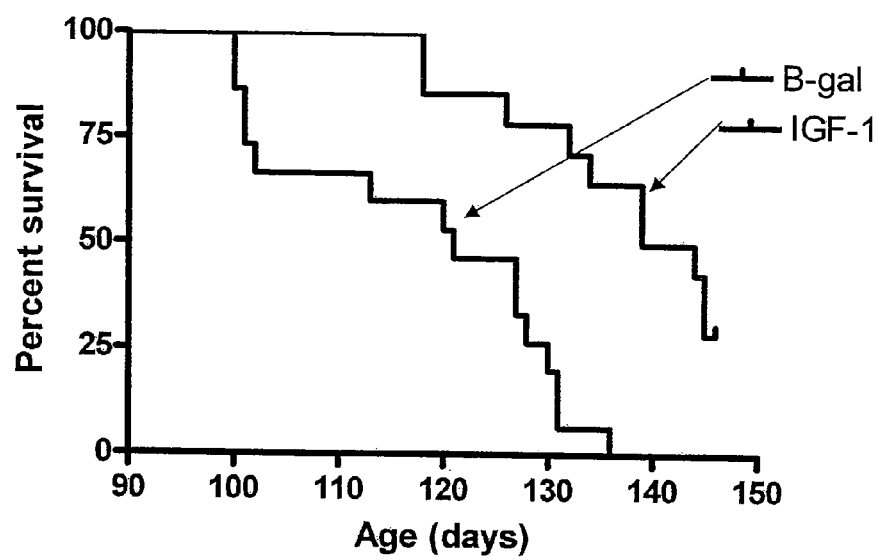
FIG. 1 shows Kaplan-Meier survival curves comparing intraventricular administration of AAV4 encoding beta-galactosidase to AAV4 encoding IGF1. A significant difference in survival was observed. Recipients were SOD mice.
Figure 2:
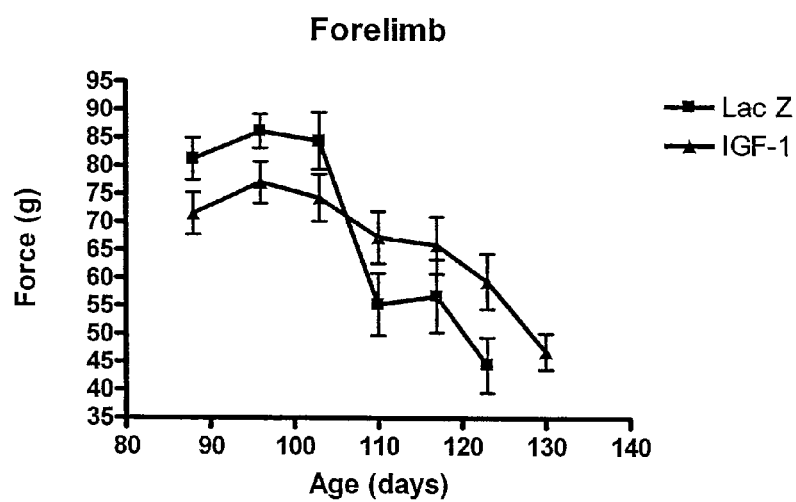
FIG. 2 shows a comparison of forelimb strength between SOD mice which received intraventricular administration of AAV4 encoding beta-galactosidase (Lac Z) versus AAV4 encoding IGF1. IGF1 recipients lost strength more gradually and more slowly.
Figure 3:
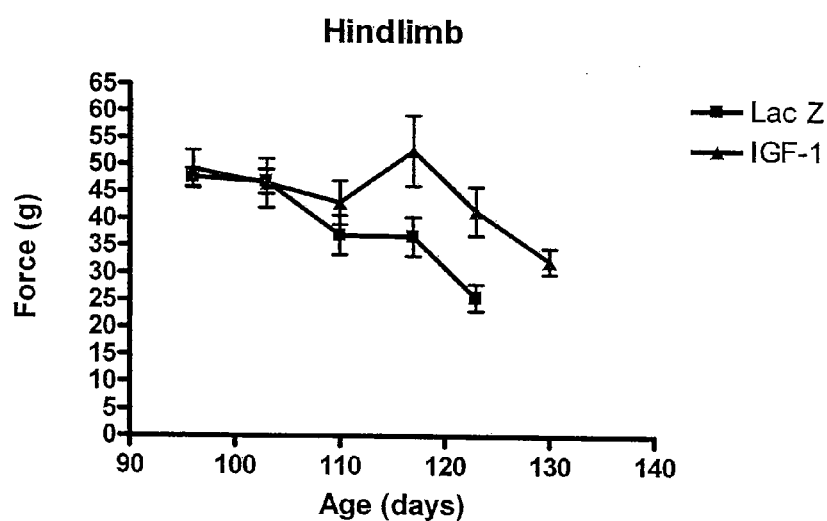
FIG. 3 shows a comparison of hindlimb strength between SOD mice which received intraventricular administration of AAV4 encoding beta-galactosidase (Lac Z) versus AAV4 encoding IGF1. IGF1 recipients lost strength more gradually and later.
Figure 4:
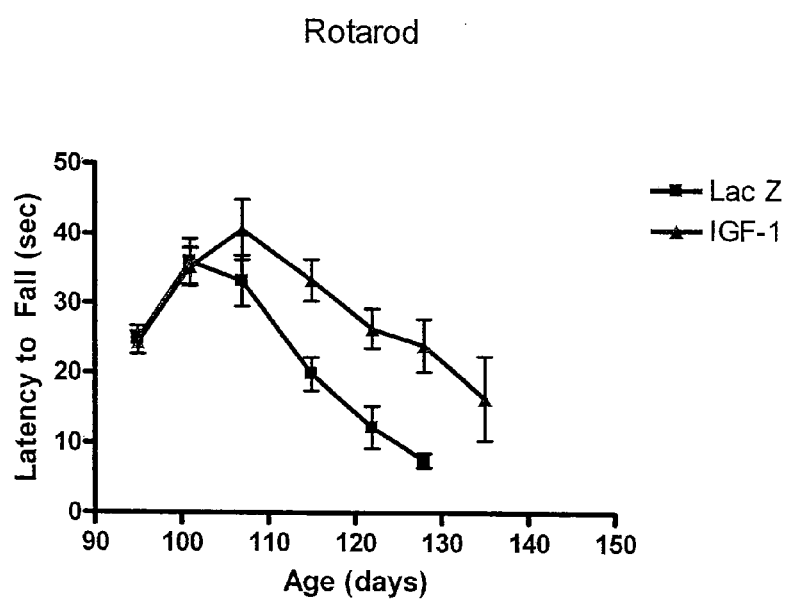
FIG. 4 shows a comparison of rotarod (latency to fall) between SOD mice which received intraventricular administration of AAV4 encoding beta-galactosidase (Lac Z) versus AAV4 encoding IGF1. IGF1 recipients declined more gradually and later.
Figure 5:
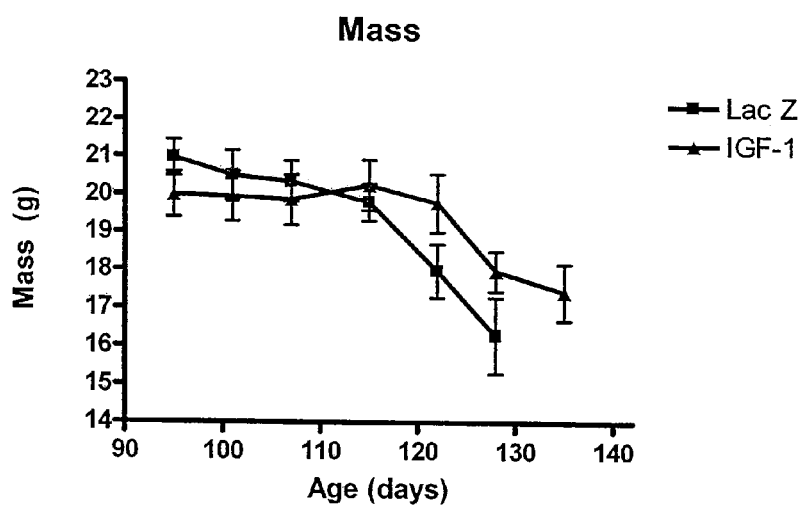
FIG. 5 shows a comparison of loss of body mass between SOD mice which received intraventricular administration of AAV4 encoding beta-galactosidase (Lac Z) versus AAV4 encoding IGF1. IGF1 recipients lost body mass more gradually and later.

Tables 1-3 provide a number of potential gene pairs for use in the instant invention where the embodiment utilizes more than one gene.

DETAILED DESCRIPTION OF THE INVENTION

In order that the present invention may be more readily understood, certain terms are first defined. Additional definitions are set forth throughout the detailed description.

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "transgene" refers to a polynucleotide that is introduced into a cell of and is capable of being transcribed into RNA and optionally, translated and/or expressed under appropriate conditions. In one aspect, it confers a desired property to a cell into which it was introduced, or otherwise leads to a desired therapeutic or diagnostic outcome.

The terms "genome particles (gp)," or "genome equivalents," or "genome copies" (gc) as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of an RNA, DNA or expression product of DNA and/or RNA that results in prevention or delay of onset or amelioration of symptoms of in a subject or an attainment of a desired biological outcome, such as correction of neuropathology, e.g., cellular pathology associated with a motor neuronal disease such as ALS. The term "therapeutic correction" refers to that degree of correction that results in prevention or delay of onset or amelioration of symptoms in a subject. The effective amount can be determined by known empirical methods.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provision that they be acceptable for use in vivo. For examples of carriers, stabilizers and adjuvants, see Martin REMINGTON'S PHARM. SCl., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998). Carriers may also comprise artificial cerebrospinal fluid (aCSF).

A "subject," "individual" or "patient" is used interchangeably herein, which refers to a vertebrate, preferably a mammal, more preferably a human. Mammals include, but are not limited to, murines, rats, simians, humans, farm animals, sport animals, and pets.

A "control" is an alternative subject or sample used in an experiment for comparison purpose. A control can be "positive" or "negative." For example, where the purpose of the experiment is to determine a correlation of an altered expression level of a gene with a particular type of pathology (see ALS, for example, infra), it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is at least 1.5 times, or at least 2.5 times, or alternatively at least 5 times, or alternatively at least 10 times higher or lower than the expression level detected in a control sample. The term "differentially expressed" also refers to nucleotide sequences in a cell or tissue which are expressed where silent in a control cell or not expressed where expressed in a control cell.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of a disease or disorder by making them more bearable.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Stereotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Stereotaxic Coordinates, 2nd ed., Academic Press, 2000.

Intracerebroventricular, or intraventricular, delivery of a recombinant viral vector may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adults, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infants. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those which reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

In one aspect, the invention provides a method to deliver a transgene to the brain of a subject by intraventricular administration of a recombinant neurotrophic viral vector containing the IGF-1 transgene. The delivery is under conditions that favor expression of the transgene in ependymal cells.

In another aspect, the invention provides a method of delivering a therapeutic transgene product to a target cell of the CNS, which is a neuron or a glial cell, in a mammal afflicted with a motor neuronal disorder, e.g., ALS or traumatic spinal cord injury, where the transgene may be IGF-1. The transgene can be administered via a neurotrophic virus. The virus can be administered via the ventricles. Ependymal cells may be transduced to express the transgene and secrete the encoded protein product.

In an alternate embodiment, the invention is a method to treat a motor neuron disorder in a subject by intraventricular administration of a recombinant neurotrophic viral vector containing a therapeutic transgene to the brain of the subject, wherein the transgene is expressed in a therapeutically effective amount in the subject.

This invention also is a method to ameliorate the symptoms of a motor neuron disorder in a subject by intraventricular administration of a recombinant neurotrophic viral vector containing a therapeutic transgene to the brain, wherein said transgene is expressed in a therapeutically effective amount in the subject.

Suitable neurotrophic viral vectors for the practice of this invention include, but are not limited to adeno-associated viral vectors (AAV), herpes simplex viral vectors (U.S. Pat. No. 5,672,344) and lentiviral vectors.

In the methods of the invention, AAV of any serotype can be used. The serotype of the viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10(26):3075-81).

AAV vectors are derived from single-stranded (ss) DNA parvoviruses that are nonpathogenic for mammals (reviewed in Muzyscka (1992) Curr. Top. Microb. Immunol., 158:97-129). Briefly, recombinant AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV4. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888. Additional exemplary AAV vectors are recombinant AAV2/1, AAV2/2, AAV2/5, AAV2/7 and AAV2/8 serotype vectors encoding human protein.

In certain methods of the invention, the vector comprises a transgene operably linked to a promoter. The transgene encodes a biologically active molecule, expression of which in the CNS results in at least partial correction of neuropathology and/or stabilization of disease progression. The transgene may be insulin growth factor-1 (IGF-1), calbindin D28, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen.

In certain methods of the invention, the vector comprises more than one transgene, wherein each transgene is operably linked to a promoter to enable the expression of more than one trangene from a single AAV vector. In additional methods, the transgenes may be operably linked to the same promoter. Each transgene encodes a biologically active molecule, expression of which in the CNS results in at least partial correction of neuropathology. Additionally, in cases where more than one transgene is delivered, the transgenes may be delivered via more than one AAV vector, wherein each AAV vector comprises a transgene operably linked to a promoter. The transgenes may be selected from the group consisiting of insulin growth factor-1 (IGF-1), calbindin D28, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, and placenta lactogen. For example, the transgenes may comprise VEGF, such as VEGF165, and IGF-1.

The insulin-like growth factor (IGF-1) gene has a complex structure, which is well-known in the art. It has at least two alternatively spliced mRNA products arising from the gene transcript. There is a 153 amino acid peptide, known by several names including IGF-1A or IGF-1Ea, and a 195 amino acid peptide, known by several names including IGF-1B or IGF-1Eb. The Eb form may also be known as Ec in humans. The mature form of IGF-1 is a 70 amino acid polypeptide. Both IGF-1Ea and IGF-1Eb contain the 70 amino acid mature peptide, but differ in the sequence and length of their carboxyl-terminal extensions. The peptide sequences of IGF-1Ea and IGF-1Eb are represented by SEQ ID NOS: 1 and 2, respectively. The genomic and functional cDNAs of human IGF-1, as well as additional information regarding the IGF-1 gene and its products, are available at Unigene Accession No. NM_00618. The IGF-1 protein may have the sequence shown in SEQ ID NO: 3 or allelic variants thereof. Allelic variants may differ by a single or a small number of amino acid residues, typically less than 5, less than 4, less than 3 residues. The IGF-1 protein sequence may be modified to contain the TAT transduction domain (YGRKKRRQRRR) as shown in SEQ ID NO: 4.

Although their functions are not fully known, calbindin D28K (also referred to as calbindin D28) and parvalbumin are calcium-binding proteins theorized to be involved in calcium buffering. Without being limited as to theory, there is evidence to suggest that calcium homeostasis is altered in subjects with ALS. There is evidence to suggest that low levels of calbindin-D28K and/or parvalbumin may increase the vulnerability of motor neurons in ALS by reducing their ability to handle an increased calcium load. This reduction may lead to cell injury and eventual motor neuron death. Further evidence suggests that neurons rich in calcium-binding proteins, such as calbindin D28K and parvalbumin, are resistant to degeneration.

HIF-1 is a heterodimeric protein composed of two subunits: (i) a constitutively expressed beta (β) subunit also known as aryl hydrocarbon nuclear translocator (ARNT) (which is shared by other related transcription factors (e.g., the dioxin/aryl hydrocarbon receptor (DR/AhR)); and (ii) an alpha (α) subunit (see, e.g., WO 96/39426; International Application No. PCT/US96/10251 describing the recent affinity purification and molecular cloning of HIF-1 a) whose accumulation is regulated by a post-translational mechanism such that high levels of the alpha subunit can only be detected during hypoxic conditions. Both subunits are members of the basic helix-loop-helix (bHLH)-PAS family of transcription factors. These domains regulate DNA binding and dimerization. The transactivation domain resides in the C-terminus of the protein. The basic region consists of approximately 15 predominantly basic amino acids responsible for direct DNA binding. This region is adjacent to two amphipathic a helices, separated by a loop of variable length, which forms the primary dimerization interface between family members (Moore, A. W., et al., Proc. Natl. Acad. Sci. USA 97:10436-41 (2000)). The PAS domain, which is named after the first three proteins in which it was identified (Per, ARNT and Sim), encompasses 200-300 amino acids containing two loosely conserved, largely hydrophobic regions approximately 50 amino acids, designated PAS A and PAS B. The HIF-1α subunit is unstable during normoxic conditions, overexpression of this subunit in cultured cells under normal oxygen levels is capable of inducing expression of genes normally induced by hypoxia. An alternative strategy would be to modify the HIF-1α subunit such that it no longer is destabilized by normoxic conditions and would therefore be more potent under a range of oxygen conditions. Replacement of the C terminal (or transactivation) region of the hypoxia-inducible factor protein with a strong transactivation domain from a transcriptional activator protein such as, for example, Herpes Simplex Virus (HSV) VP16, NFκB or yeast transcription factors GAL4 and GCN4, is designed to stabilize the protein under normoxic conditions and provide strong, constitutive, transcriptional activation. To stabilize the hypoxia-inducible factor protein under normoxic conditions and to provide strong, constitutive transcriptional activation, a hybrid/chimeric fusion protein consisting of the DNA-binding and dimerization domains from HIF-1α and the transactivation domain from Herpes Simplex Virus (HSV) VP16 protein was constructed. Administration of this hybrid/chimera to the cells of a subject via gene therapy induces the expression of genes normally up-regulated in response to hypoxia (i.e., VEGF and the like). A constitutively stable hybrid HIF-1α has been shown to be effective for treating ischemic patients (U.S. Pat. Nos. 6,432,927 and 7,053,062, both of which are incorporated by reference herein in their entirety).

Members of the vascular endothelial growth factor (VEGF) family are among the most powerful modulators of vascular biology. They regulate vasculogenesis, angiogenesis, and vascular maintenance. VEGF 165 is one such member of the VEGF family that may be used in the instant invention.

The molecular basis of spinal muscular atrophy (SMA), an autosomal recessive neuromuscular disorder, is the homozygous loss of the survival motor neuron gene 1 (SMN1). A nearly identical copy of the SMN1 gene, called SMN2, modulates the disease severity. The functional difference between both genes is a translationally silent mutation that, however, disrupts an exonic splicing enhancer causing exon 7 skipping in most SMN2 transcripts. Only 10% of SMN2 transcripts encode functional full-length protein identical to SMN1. SMN protein plays a well-established role in assembly of the spliceosome and may also mediate mRNA trafficking in the axon and nerve terminus of neurons.

CNTF (Ciliary neurotrophic factor) is a neurocytokine expressed by glial cells in peripheral nerves and the central nervous system. CNTF is generally recognized for its function in support and survival of non-neuronal and neuronal cell types. See e.g., Vergara, C and Ramirez, B; Brain Res, Brain Res. Rev. 2004; 47: 161-73.

Sonic hedgehog (Shh) controls important developmental processes, including neuronal and glial cell survival.

Erythropoietin (EPO) is a principal regulator of erythroid progenitor cells. However, it is functionally expressed in the nervous system and has been reported to have a neuroprotective effects. See e.g., Bartesaghi, S., 2005. Neurotoxicology, 26:923-8.

Lysyl oxidase (LOX) oxidizes the side chain of peptidyl lysine thereby converting certain lysine residues to alpha-aminoadipic-delta-semialdehyde. This is a post-translational change that, for example, enables the covalent cross-linking of the component chains of collagen and elastin. It stabilizes the fibrous deposits of these proteins in the extracellular matrix. LOX can also oxidize lysine within a variety of cationic proteins, which suggests that its functions are broader than stabilization or the extracellular matrix. LOX is synthesized as a preprotein; it emerges from the cell as proLOX and is processed proteolytically to the active enzyme. See e.g., Lucero, H A and Kagan, H M, Cell Mol. Life. Sci. 2006; 63(19-20):2304-16.

Progranulin (PGRN) is a pleitropic protein that has gained the attention of the neuroscience community with the recent discoveries of mutations in the gene that cause frontotemporal lobar degeneration. PGRN in the central nervous system is expressed by microglia and neurons and plays a role in brain development. PGRN is also involved in multiple "tissue modeling" processes including development, wound repair and tumorogenesis. PGRN is converted to Granulin (GRN) by elastase enzymes. While progranulin has trophic properties, GRNs are more akin to inflammatory mediators. Gene expression studies from animal models of CNS disease show a differential increase in PRGN combined with microglial activation and inflammation. Suggestion that the increase in PGRN expression is closely related to microglial activation and neuroinflammation. Moreover, PGRN expression is increased in activated microglia in many neurodegenerative diseases including motor neuron disease and Alzheimer's disease. Studies have identified mutations in PGRN as a cause of neurodegenerative disease and indicate the importance of PGRN function for neuronal survival.

Prolactin and placenta lactogen: Oligodendrocytes, the myelinating cells of the CNS, continue to be generated by oligodendrocyte precursor cells (OPCS) throughout adulthood (Gensert and Goldman, 1997; Levison et al., 1999; Menn et al., 2006; Peters and Sethares, 2004) and are required for the intrinsic repair of myelin damage in the adult CNS (Polito and Reynolds, 2005). The physiological events that modulate OPC proliferation and the generation of new myelinating oligodendrocytes in the adult CNS are largely known.

Recently it has been reported that patients with Multiple Sclerosis, a demyleinating disease, have a reduced relapse rate during the 3rd trimester of pregnancy suggesting that hormones influence oligodendrocyte generation (Confavreux et al., 1998; Voskuhl, 2003). Remission in MS patients is correlated with a decrease in the number and size of active white matter lesions (van Walderveen et al., 1994). Interestingly, pregnancy in mice results in an increase in the generation of new oligodendrocytes and the number of myelinated axons within the maternal CNS (Gregg et al., 2007). Prolactin, a hormone that plateaus during the final stage of pregnancy, has been shown to regulate OPC proliferation during pregnancy and promote white matter repair in virgin female mice (Gregg et al., 2007).

There is reason to believe that human placenta lactogen (hPL), a hormone that also peaks during the 3rd trimester of pregnancy (Selenkow et al., 1969), may have a similar influence on oligodendrocyte generation. hPL has a number of biological activities that are qualitatively similar to human growth hormone (hGH) and prolactin (Lesniak et al., 1977) and appears to be a major regulator of IGF-1 production (Handwerger et al., 1992; Zimkeller, 2000; Handwerger et al., 2000). Both hGH and IGF-1 have been shown to be stimulators of myelination in the adult CNS (Carson et al., 1993; Peltwon et al., 1977). Therefore, the treatment of CNS diseases involving demyelination such as MS, ALS, stroke and spinal cord injury may benefit from PRL or hPL based therapies intraventricular injection of an rhPRL or hPL expressing viral vector.

Ghrelin is a gastric hormone that was recognized in 1999 as a mediator of growth hormone release. See e.g. Wu, J T et al., 2004; Ann. Surg. 239:464.

Neuroserpin is a serpin protease inhibitor family member. In certain central nervous system conditions, neuroserpin can play a neuroprotective role potentially through the blockage of the effects of tPA. See, e.g., Galliciotti, G and Sonderegger, P, 2006, Front Biosci 11: 33; Simonin, Y et al., 2006, J Neurosci; 26:10614; Miranda, E and Lomas, D A, 2006, Cell Mol Life Sci 63:709.

Angiogenin is a member of the RNAse superfamily. It is a normal constituent of circulation but has also been implicated as a risk factor in motor neuron disorders.

Without being limited as to theory, IGF-1 is a therapeutic protein for the treatment of ALS due to its many actions at different levels of neuraxis (see Dore et al., Trends Neurosci, 1997, 20:326-331). In the brain: It is thought to reduce both neuronal and glial apoptosis, protect neurons against toxicity induced by iron, colchicine, calcium destabilizers, peroxides, and cytokines. It also is thought to modulate the release of neurotransmitters acetylcholine and glutamate. It is also thought to induce the expression of neurofilament, tublin, and myelin basic protein. In the spinal cord: IGF-1 is thought to modulate ChAT activity and attenuate loss of cholinergic phenotype, enhance motor neuron sprouting, increase myelination, inhibit demyelination, stimulate motor neuron proliferation and differentiation from precursor cells, and promote Schwann cell division, maturation, and growth. In the muscle: IGF-1 is thought to induce acetylcholine receptor cluster formation at the neuromuscular junction and increase neuromuscular function and muscle strength.

The level of transgene expression in eukaryotic cells is largely determined by the transcriptional promoter within the transgene expression cassette. Promoters that show long-term activity and are tissue- and even cell-specific are used in some embodiments. Non limiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), GFAP promoter (Xu et al. (2001) Gene Ther. 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277), the β-glucuronidase (GUSB) promoter (Shipley et al. (1991) Genetics 10:1009-1018), and ubiquitin promoters such as those isolated from human ubiquitin A, human ubiquitin B, and human ubiquitin C as described in U.S. Pat. No. 6,667,174. To prolong expression, other regulatory elements may additionally be operably linked to the transgene, such as, e.g., the Woodchuck Hepatitis Virus Post-Regulatory Element (WPRE) (Donello et al. (1998) J. Virol. 72:5085-5092) or the bovine growth hormone (BGH) polyadenylation site.

For some CNS gene therapy applications, it may be necessary to control transcriptional activity. To this end, pharmacological regulation of gene expression with viral vectors can been obtained by including various regulatory elements and drug-responsive promoters as described, for example, in Habermae et al. (1998) Gene Ther. 5:1604-16011; and Ye et al. (1995) Science 283:88-91.

In certain embodiments, the concentration or titer of the vector in the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^9$ to/ml); or (c) 5, 6, 7, 8, 9, 10, 15, 20, 25, or 50 ($\times 10^{10}$ iu/ml).

In one aspect, the transgene encodes a biologically active molecule, expression of which in the CNS results in at least partial correction of neuropathology and/or stabilization of disease progression. In some embodiments, the therapeutic transgene product is an IGF-1 protein that alleviates and/or prevents the symptoms of ALS. See Roaul et al. (2005) Nat. Med. 11(4):423-428 and Ralph et al. (2005) Nat. Med. 11(4): 429-433. In other aspects, two transgenes are encoded, for example IGF-1 and VEGF, expression of which in the CNS results in at least partial correction of neuropathology such as alleviation and/or prevention and/or stabilization and/or slowing the progression of the symptoms of ALS.

In one aspect when performing these methods, the transgene expresses a therapeutic amount of insulin growth factor-1 (IGF-1), calbindin D28, parvalbumin, HIF1-alpha, SIRT-2, VEGF, SMN-1, SMN-2, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Stereotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Stereotaxic Coordinates, 2nd ed., Academic Press, 2000.

To deliver the solution or other composition containing the viral vector specifically to a particular region of the central nervous system, such as to a particular ventricle, e.g., to the lateral ventricles or to the fourth ventricle of the brain, it may be administered by stereotaxic microinjection. For example, on the day of surgery, patients will have the stereotaxic frame base fixed in place (screwed into the skull). The brain with stereotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector solution in a pharmaceutically acceptable carrier will then be injected. Additional routes of administration may be used, e.g., superficial cortical application under direct visualization, or other non-stereotaxic application.

One way for delivering the viral vector is to use a pump. Such pumps are commercially available, for example, from Alzet (Cupertino, Calif.) or Medtronic (Minneapolis, Minn.). The pump may be implantable. Another convenient way to administer the vector is to use a cannula or a catheter.

The subject invention provides methods to modulate, correct or augment motor function in a subject afflicted with motor neuronal damage. For the purpose of illustration only, the subject may suffer from one or more of amytrophic lateral sclerosis (ALS), spinal bulbar muscular atrophy, spinal muscular atrophy, spinal cerebellar ataxia, primary lateral sclerosis (PLS), or traumatic spinal cord injury.

Without being limited as to theory, the pathology associated with motor neuron damage may include motor neuron degeneration, gliosis, neurofilament abnormalities, loss of myelinated fibers in corticospinal tracts and ventral roots. Two types of onset are recognized: bulbar onset, which affects brainstem motor neurons, (affects the facial muscles, speech, and swallowing); and limb onset, which affects spinal cord motor neurons, is reflected by spasticity, generalized weakness, muscular atrophy, paralysis, and respiratory failure. In ALS, subjects have both bulbar and limb onset. In PLS, subjects have bulbar onset.

The ability to organize and execute complex motor acts depends on signals from the motor areas in the cerebral cortex, i.e., the motor cortex. Cortical motor commands descend in two tracts. The corticobular fibers control the motor nuclei in the brain stem that move facial muscles and the corticospinal fibers control the spinal motor neurons that innervate the trunk and limb muscles. The cerebral cortex also indirectly influences spinal motor activity by acting on the descending brain stem pathways.

The primary motor cortex lies along the precentral gyrus in Broadmann's area (4). The axons of the cortical neurons that project to the spinal cord run together in the corticospinal tract, a massive bundle of fibers containing about 1 million axons. About a third of these originate from the precentral gyms of the frontal lobe. Another third originate from area 6. The remainder originates in areas 3, 2, and 1 in the somatic sensory cortex and regulate transmission of afferent input through the dorsal horn.

The corticospinal fibers run together with corticobulbar fibers through the posterior limb of the internal capsule to reach the ventral portion of the midbrain. They separate in the pons into small bundles of fibers that course between the pontine nuclei. They regroup in the medulla to form the medullary pyramid. About three-quarters of the corticospinal fibers cross the midline in the pyramidal decussation at the junction of the medulla and spinal cord. The crossed fibers descend in the dorsal part of the lateral columns (dorsolateral column) of the spinal cord, forming the lateral corticospinal tract. The uncrossed fibers descend in the ventral columns as the ventral corticospinal tract.

The lateral and ventral divisions of the corticospinal tract terminate in about the same regions of spinal gray matter as the lateral and medial systems of the brain stem. The lateral corticospinal tract projects primarily to motor nuclei in the lateral part of the ventral horn and to interneurons in the intermediate zone. The ventral corticospinal tract projects bilaterally to the ventromedial cell column and to adjoining portions of the intermediate zone that contain the motor neuorons that innervate axial muscles.

If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyms, and they terminate in the outer two-thirds of the molecular layer of the dentate gyms. The axons from layer III cells project bilaterally to the cornu ammonis areas CA1 and CA3 of the hippocampus, terminating in the stratum lacunose molecular layer.

In one aspect, the disclosed methods include administering to the CNS of an afflicted subject a neurotrophic viral vector carrying a transgene encoding a therapeutic product and allowing the transgene to be expressed within the CNS near the administration site at a level sufficient to exert a therapeutic effect as the expressed protein is transported via the CSF throughout the CNS. In addition, the vector may comprise a polynucleotide encoding for a biologically active molecule effective to treat the CNS disorder. Such biologically active molecules may comprise peptides including but not limited to native or mutated versions of full-length proteins, native or mutated versions of protein fragments, synthetic polypeptides.

In an illustrative embodiment, the administration is accomplished by direct injection of a high titer vector solution into one or more of the ventricular spaces of the brain, such as the lateral ventricle of a subject or patient. For example, the administration is by direct bolus injection into one or more ventricles of the brain such as the lateral and fourth ventricles.

In some embodiments, the methods comprise administration of a high titer neurotrophic vector carrying a therapeutic transgene so that the transgene product is expressed at a therapeutic level at a first site within the CNS distal to the ultimate site of action of the expressed product. In some embodiments, the viral titer of the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^9$ tu/ml); or (c) 5, 6, 7, 8, 9, 10, 15, 20, 25, or 50 ($\times 10^{10}$ iu/ml).

In experimental mice, the total volume of injected AAV solution is for example, between 1 to 20 μl. For other mammals, including the human brain, volumes and delivery rates are appropriately scaled. For example, it has been demonstrated that volumes of 150 μl can be safely injected in the primate brain (Janson et al. (2002) Hunt. Gene Ther. 13:1391-1412). Treatment may consist of a single injection per target site, or may be repeated in one or more ventricles. Suitable ventricles include the lateral ventricles, third ventricle, and the fourth ventricle. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Titration of Recombinant Vectors

AAV vector titers are measured according to genome copy number (genome particles per milliliter). Genome particle concentrations are based on Taqman® PCR of the vector DNA as previously reported (Clark et al. (1999) Hum. Gene Ther., 10:1031-1039; Veldwijk et al. (2002) Mol. Ther., 6:272-278).

Vectors carrying an assayable marker gene such as the β-galactosidase (Lac Z) or green fluorescent protein gene (GFP) can be titered using an infectivity assay. Susceptible cells (e.g., HeLa, or COS cells) are transduced with the AAV and an assay is performed to determine gene expression such as staining of β-galactosidase vector-transduced cells with X-gal (5-bromo-4-chloro-3-indolyl-β-D-galactopyranoside) or fluorescence microscopy for GFP-transduced cells. For example, the assay is performed as follows: $4\times10^4$ HeLa cells are plated in each well of a 24-well culture plate using normal growth media. After attachment, i.e., about 24 hours later, the cells are infected with Ad type 5 at a multiplicity of infection (MOI) of 10 and transduced with serial dilutions of the packaged vector and incubated at 37° C. One to three days later, before extensive cytopathic effects are observed, the appropriate assay is performed on the cells (e.g., X-gal staining or fluorescence microscopy). If a reporter gene such as β-galactosidase is used, the cells are fixed in 2% paraformaldehyde, 0.5% glutaraldehyde and stained for β-galactosidase activity using X-gal. Vector dilutions that give well-separated cells are counted. Each positive cell represents 1 transduction unit (tu) of vector.

Therapeutically Relevant Model of Amyotrophic Lateral Sclerosis (ALS).

Amytrophic lateral sclerosis (ALS) is a fatal neurodegenerative disease that is characterized by a selective loss of motor neurons in the cortex, brain stem and spinal cord. Progression of the disease can lead to atrophy of limb, axial and respiratory muscles. Motor neuron cell death is accompanied by reactive gliosis, neurofilament abnormalities, and a significant loss of large myelinated fibers in the corticospinal tracts and ventral roots[1-6]. Although the etiology of ALS is poorly understood, accumulating evidence indicates that sporadic (SALS) and familial (FALS) ALS share many similar pathological features; thus, providing a hope that the study of either form will lead to a common treatment[7]. FALS accounts for approximately 10% of diagnosed cases, of which 20% are associated with dominantly inherited mutations in Cu/Zn superoxide dismutase (SOD1)[8]. Transgenic mice that express the mutant human SOD1 protein (e.g., SOD1$^{G93A}$ mice) recapitulate many pathological features of ALS and are an available animal model to study ALS[9]. For SALS, a myriad of pathological mechanisms have been implicated as the underlying cause, including glutamate induced excitotoxicity, toxin exposure, proteasome dysfunction, mitochondrial damage, neurofilament disorganization and loss of neurotrophic support[10,11].

To date there is no effective therapy for the treatment of ALS. Neurotrophic factors such as insulin growth factor I (IGF-1) have been investigated extensively for their potential usefulness in the treatment of ALS. Intracranial delivery of viral vectors to regions of the CNS that are interconnected with brainstem and spinal motor neurons via the CSF provides a means of administering potential therapeutics, such as IGF-1, to areas that would otherwise be difficult to target through prior art means.

Without being limited as to theory, IGF-1 is a therapeutic protein for the treatment of ALS due to its many actions at different levels of neuraxis (see Dore et al., Trends Neurosci, 1997, 20:326-331). In the brain: It is thought to reduce both neuronal and glial apoptosis, protect neurons against toxicity induced by iron, colchicine, calcium destabilizers, peroxides, and cytokines. It also is thought to modulate the release of neurotransmitters acetylcholine and glutamate. It is also thought to induce the expression of neurofilament, tublin, and myelin basic protein. In the spinal cord: IGF-1 is thought to modulate ChAT activity and attenuate loss of cholinergic phenotype, enhance motor neuron sprouting, increase myelination, inhibit demyelination, stimulate motor neuron proliferation and differentiation from precursor cells, and promote Schwann cell division, maturation, and growth. In the muscle: IGF-1 is thought to induce acetylcholine receptor cluster formation at the neuromuscular junction and increase neuromuscular function and muscle strength. In the following experiments, the IGF-1Ea form of the protein was utilized.

Example 1

Intracerebroventricular Delivery of AAV4-IGF-1

We conducted experiments to determine if intraventricular delivery of AAV4-IGF-1 led to (1) significant extension of lifespan; (2) improved performance on rotarod and grip strength tasks; and (3) reduced neuropathology (i.e., alleviation in gliosis and improved motor neuron survival) in the brainstem and spinal cord.

Symptomatic SOD1 mice (i.e., 90 days old) were treated either with AAV4-IGF-1 or AAV4-Bgal control vector (Bgal is also referred to as Lac Z). For each mouse, vectors were injected into both the lateral (A-P: −0.3 from bregma, M-L: −1.0 from bregma, D-V: −2.0 from dura, incisor bar: 0.0) and the 4th ventricle (A-P: −5.90 from bregma, M-L: 0.0 from bregma, D-V: −2.9 from dura, incisor bar: 0.0) using a stereotaxic frame. Vectors were delivered with a 10 µl Hamilton syringe at a rate of 0.5 µl/minute for a total of 1.80×10¹⁰ genome copies per ventricle. The final injection volume for each vector was 10 µl/ventricle. At age 110 days or at end stage, 4 mice from each treatment group were sacrificed for histological analysis (i.e., GFAP (glial fibrillary acidic protein) staining and MN counts in the brainstem and spinal cord). End points which have been evaluated include survival analysis, rotarod, hindlimb and forelimb grip strength tests, and body mass.

Testing of motor function using a rotarod device and Grip Strength Meter (Columbus Instruments, Columbus, Ohio) can begin at 70 days of age. Each weekly session may consist of three trials on the elevated accelerating rotarod beginning at 5 rpm/min. The time each mouse remains on the rod can be registered automatically. Grip strength meter testing can be performed by allowing the animals to grasp a platform followed by pulling the animal until it releases the platform: the force measurement is recorded in four separate trials. Onset of disease-related weakness is defined when one hindlimb displayed muscle weakness and limb dragging on the rotarod, as assessed by two independent observers. To determine mortality in a reliable and humane fashion, we use an artificial end point defined by the inability of mice to right themselves 30 seconds after being placed on their sides.

Intracerebroventricular delivery of AAV4-IGF-1 resulted in a significant extension of lifespan in SOD1 mice as compared to mice receiving AAV4-Bgal as a control vector. Mice receiving AAV4-IGF1 had a median survival time of 141.5 days as compared to a median survival time of 121 days in mice treated with AAV4-Bgal (FIG. 1). SOD1 mice treated with AAV4-IGF-1 had improved functional outcomes as measured by Rotarod testing, forelimb grip strength, and hindlimb grip strength as compared to control-treated mice. Results are shown in FIGS. 1-5.

Figure 6:
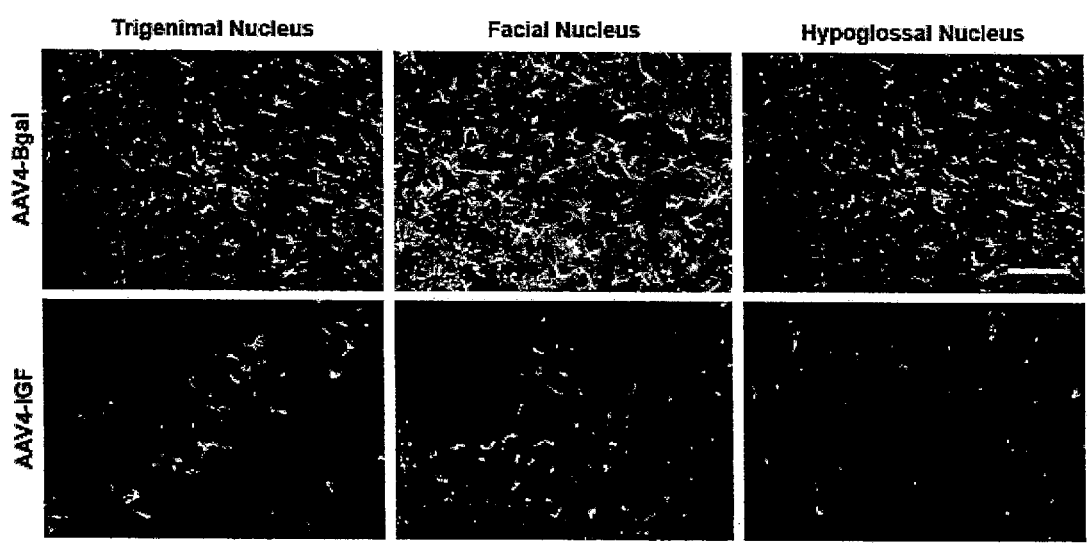
FIG. 6 shows a comparison of GFAP staining in the brainstem of SOD mice that received intraventricular administration of AAV4 encoding beta-galactosidase (Bgal) versus AAV4 encoding IGF 1. As evidenced by the reduced GFAP staining in the AAV4-IGF1 treated mice, intraventricular delivery of AAV4-IGF-1 led to a reduction in astrogliosis within the brainstem.
Figure 7:
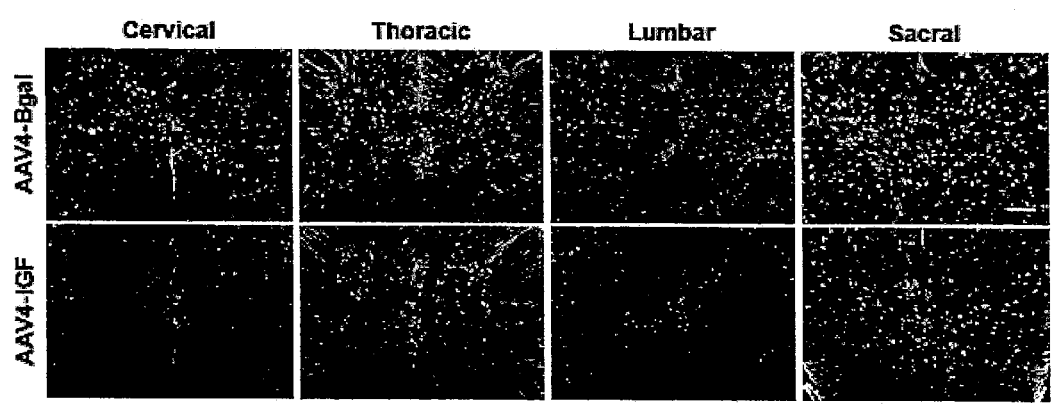
FIG. 7 shows a comparison of GFAP staining in the ventral spinal cord of SOD mice that received intraventricular administration of AAV4 encoding beta-galactosidase (Bgal) versus AAV4 encoding IGF1. As evidenced by the reduced GFAP staining in the AAV4-IGF1 treated mice, intraventricular delivery of AAV4-IGF-1 led to a reduction in astrogliosis in the ventral spinal cord.

Histological assessment of GFAP, which is a marker of gliosis and a pathological hallmark of ALS, demonstrated that astrogliosis was significantly reduced in mice treated with AAV4-IGF1 as compared to control mice treated with AAV4-Bgal. This reduction was observed in both the brainstem region of the CNS (e.g., trigeminal nucleus, facial nucleus, hypoglossal nucleus; FIG. 6) and the ventral spinal cord (e.g., cervical, thoracic, lumbar, sacral; FIG. 7).

Figure 8:
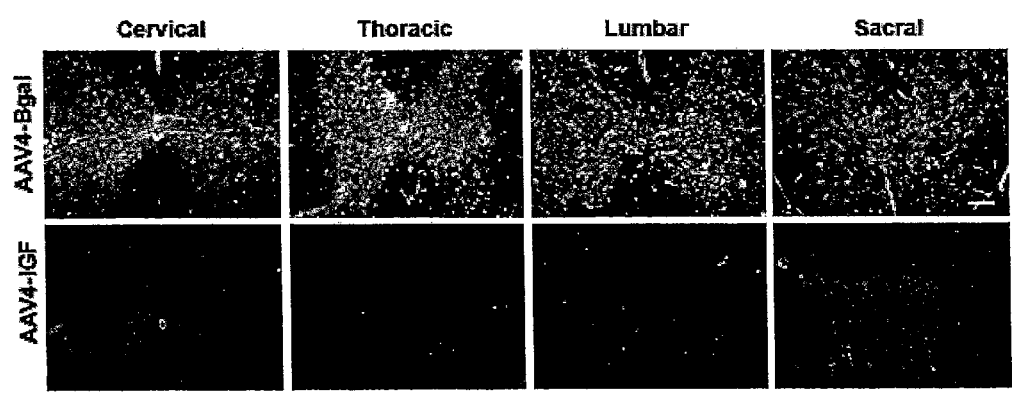
FIG. 8 shows a comparison of nitrotyrosine levels in SOD mice that received intraventricular administration of AAV4 encoding beta-galactosidase (Bgal) versus AAV4 encoding IGF1. As evidenced by the reduced staining in the AAV4-IGF1 treated mice, intraventricular delivery of AAV4-IGF-1 led to a reduction in nitrotyrosine levels throughout the spinal cord e.g., cervical, thoracic, lumbar, and sacral regions.

Histological assessment of nitrotyrosine levels, which is a marker of peroxynitrite and a pathological marker associated with ALS, demonstrated that nitrotyrosine levels were significantly reduced in mice treated with AAV4-IGF 1 as compared to control mice treated with AAV4-Bgal. This reduction in nitrotyrosine levels was observed throughout the spinal cord, e.g., cervical, thoracic, lumbar, and sacral regions (FIG. 8).

Example 2

Intracerebroventricular Delivery of AAV4-IGF-1 and AAV4-GFP

Symptomatic SOD1 mice (i.e., 88-90 days old) were treated either with AAV4-IGF-1 or AAV4-GFP vector via intracerebroventricular injection of the vector into both the lateral and the 4th ventricle. Mice received a dose of 2 e10 gc/ventricle. Green fluorescent protein was utilized as a control protein, which enabled the visualization of expression mediated by the injection of the AAV vectors.

The end points evaluated included survival, rotarod testing, grip strength (hindlimb and forelimb), motor neuron cell counts, GFP protein distribution, glial fibrillary acidic protein (GFAP) levels, nitrotyrosine levels, and RT-PCR to measure viral distribution within the CNS. At age 110 days or at end stage, mice from each treatment group were sacrificed for additional analysis. Glial fibrillary acidic protein (GFAP) levels were evaluated histologically. GFAP is a marker of gliosis, which is a pathological hallmark of ALS. Nitrotyrosine levels were evaluated histologically; nitrotyrosine is a marker of peroxynitrite.

Intracerebroventricular delivery of AAV4-IGF-1 resulted in a significant extension of lifespan in SOD1 mice as compared to mice receiving AAV4-GFP as a control vector. SOD1 mice treated with AAV4-IGF-1 had improved functional outcomes as measured by Rotarod testing, forelimb grip strength, and hindlimb grip strength as compared to control-treated mice.

Figure 9:
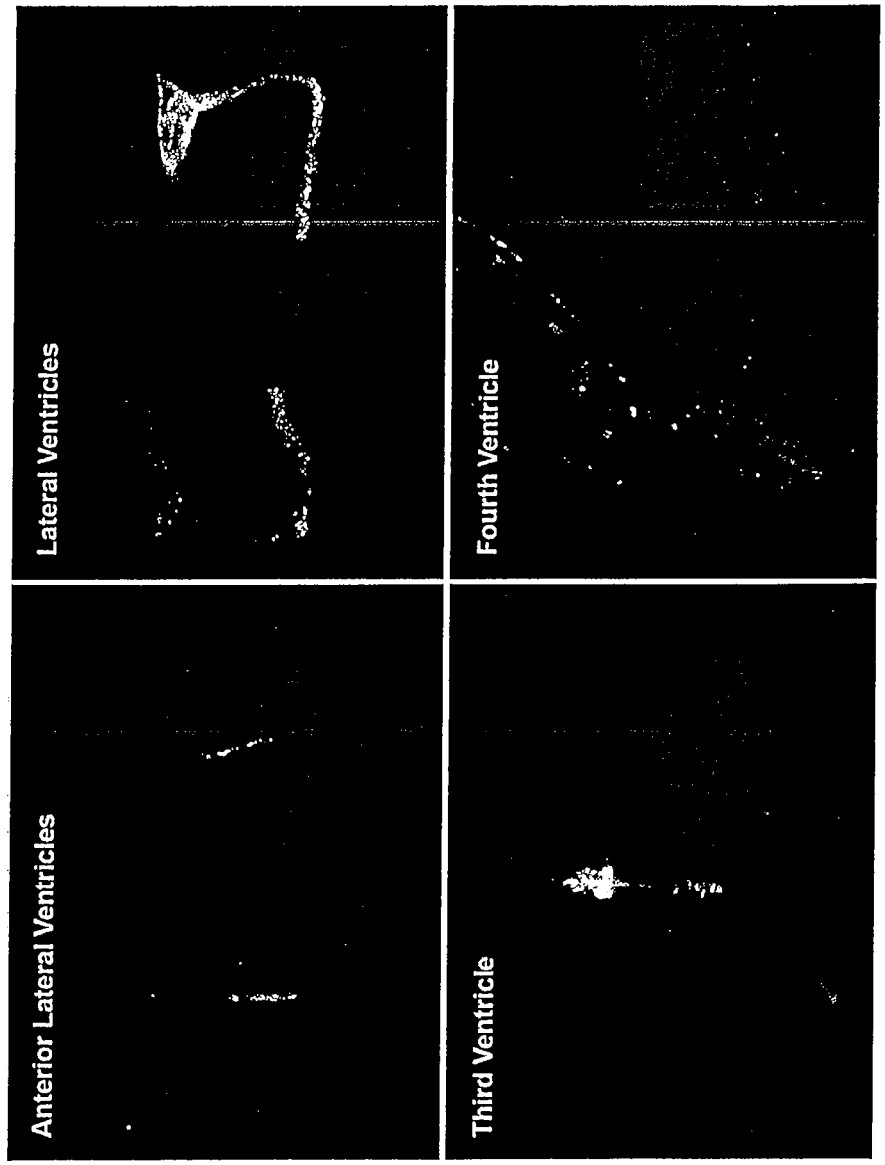
FIG. 9 shows green fluorescent protein (GFP) expression in mice treated with AAV4-GFP. GFP is distributed in the ependymal cell layer of the ventricular system following intraventricular delivery of AAV4-GFP.
Figure 10:
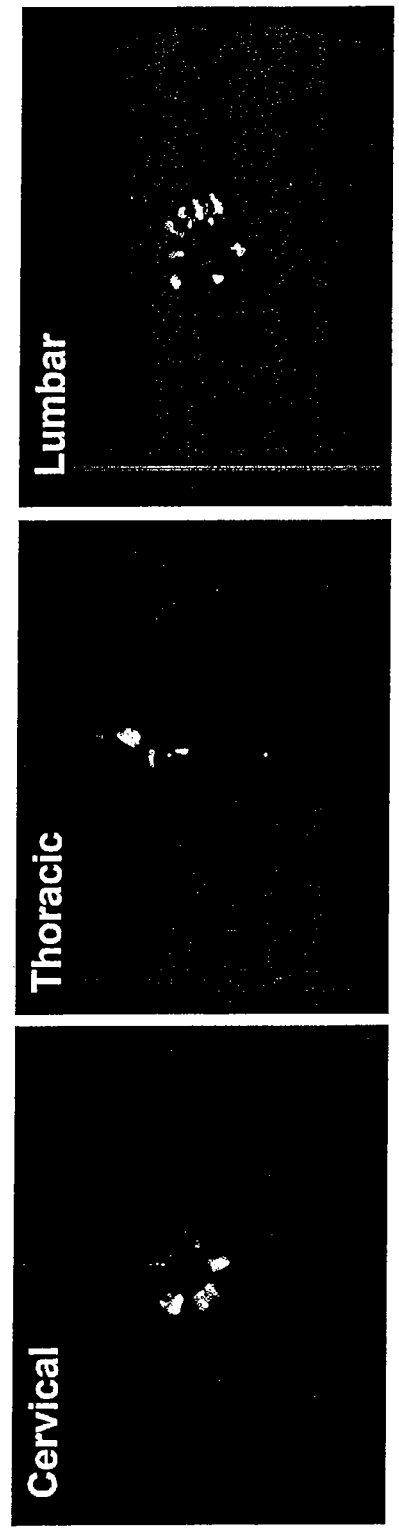
FIG. 10 shows green fluorescent protein (GFP) expression in mice treated with AAV4-GFP. GFP is distributed in the ependymal cell layer of the spinal cord central canal following intraventricular delivery of AAV4-GFP.

Visualization of green fluorescent protein (GFP) expression in mice that had been treated with AAV4-GFP indicated that GFP was distributed throughout the ependymal cell layer of the ventricular system. For example, GFP was visualized in the anterior lateral ventricles, the lateral ventricles, the third ventricle, and the fourth ventricle (FIG. 9). GFP was also visualized in the choroid plexus of the ventricular system and the ependymal cell layer of the spinal cord central canal (including the cervical, thoracic, and lumbar regions) (FIG. 10).

Figure 11:
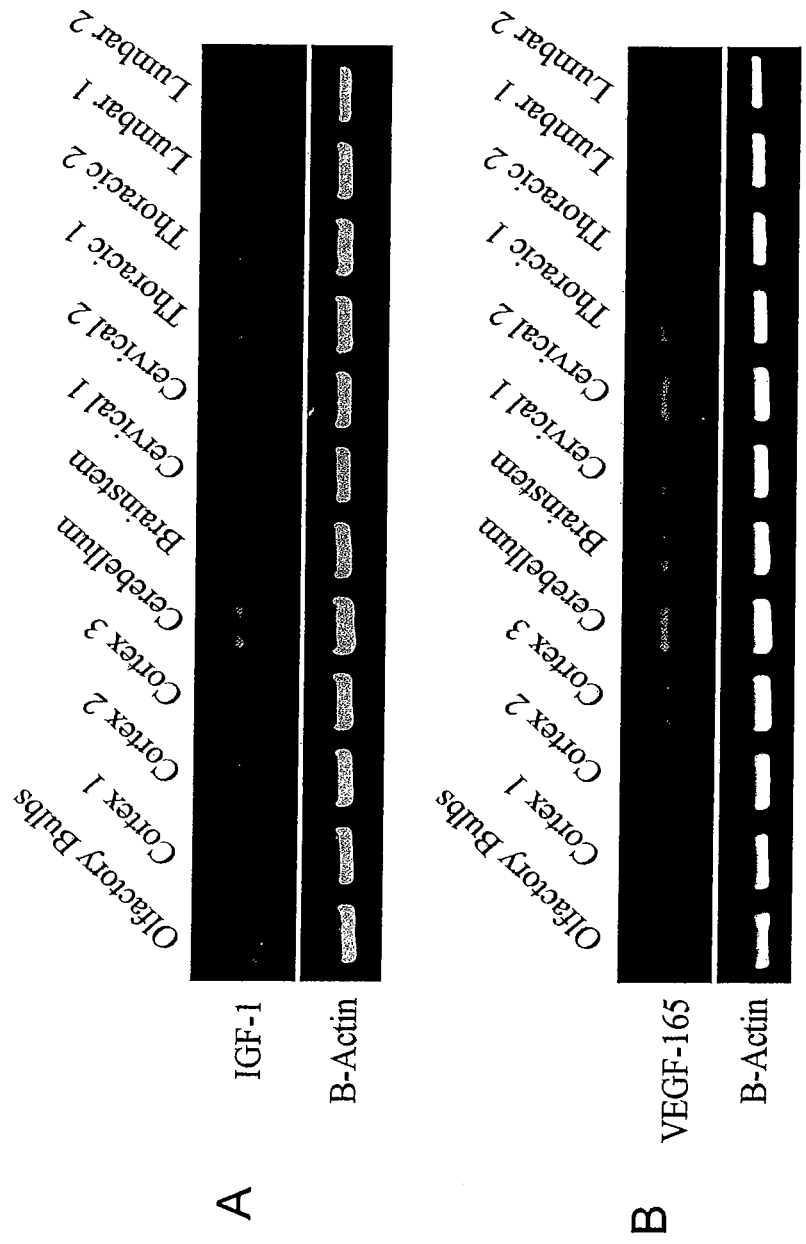
FIG. 11A shows the results of RT-PCR performed on tissues of SOD mice that were treated by intraventricular injection of AAV4-IGF-1. B-Actin was measured as an internal control. Vector was detected throughout the cortex, brainstem, and spinal cord following intraventricular delivery.
FIG. 11B shows the results of RT-PCR performed on tissues of SOD mice that were treated by intraventricular injection of AAV4-VEGF. B-Actin was measured as an internal control. Vector was detected throughout the cortex, brainstem, and spinal cord following intraventricular delivery of AAV4-VEGF.

RT-PCR for the AAV4-IGF-1 vector demonstrated that vector was present in the cortex, brainstem, and spinal cord following intraventricular delivery (FIG. 11A).

Example 3

Intracerebroventricular Delivery of AAV4-VEGF and AAV4-GFP

Symptomatic SOD1 mice (i.e., 88-90 days old) were treated either with AAV4-VEGF-165 or AAV4-GFP vector via intracerebroventricular injection of the vector into both the lateral and the 4th ventricle. Mice received a dose of 2 e10 gc/ventricle. Green fluorescent protein was utilized as a control protein, which enabled the visualization of expression mediated by the injection of the AAV vectors.

The end points evaluated included survival, rotarod testing, grip strength (hindlimb and forelimb), and RT-PCR to measure viral distribution within the CNS.

Figure 12:
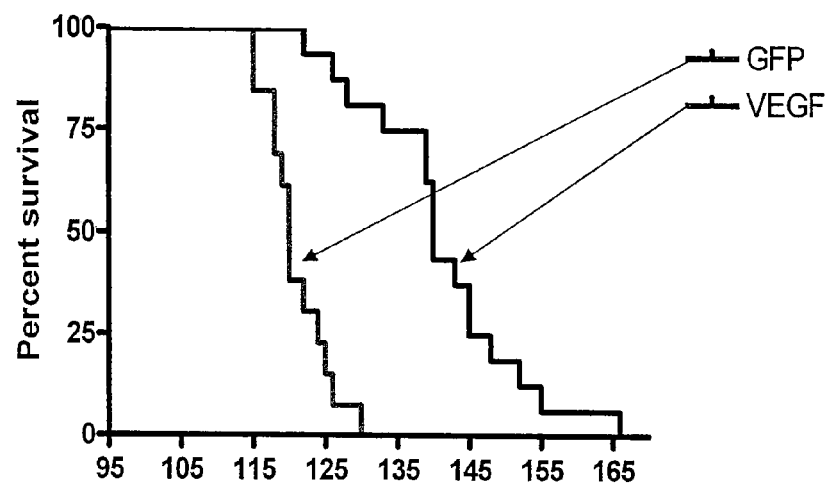
FIG. 12 shows Kaplan-Meier survival curves of SOD1 mice that received intraventricular administration of AAV4 encoding green fluorescent protein (GFP) or AAV4 encoding VEGF165. A significant increase in median survival was observed in mice receiving AAV4-VEGF.

Intracerebroventricular delivery of AAV4-VEGF resulted in a significant extension of lifespan in SOD1 mice as compared to mice receiving AAV4-GFP as a control vector. Median survival times for mice receiving AAV4-VEGF was 140 days whereas median survival times for mice receiving AAV4-GFP was 120 days (FIG. 12).

Figure 13:
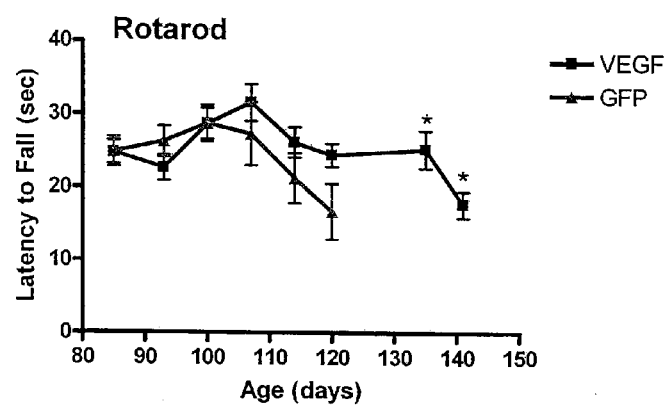
FIG. 13 shows a comparison of rotarod (latency to fall) between SOD mice that received intraventricular administration of AAV4 encoding GFP versus AAV4 encoding VEGF165. VEGF165 recipients declined more gradually and later.
Figure 13:
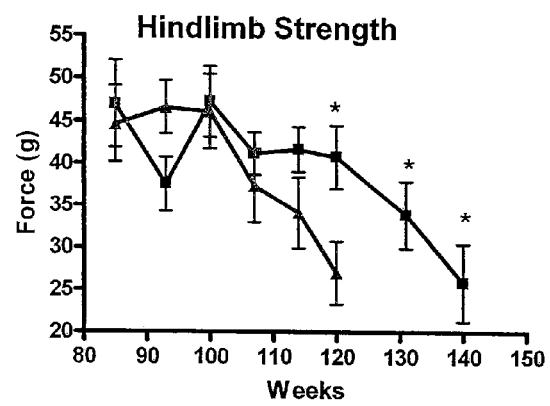

SOD1 mice treated with AAV4-VEGF had improved functional outcomes as measured by Rotarod testing (FIG. 13), forelimb grip strength and hindlimb grip strength (FIG. 13) as compared to control-treated mice.

Intraventricular delivery of AAV4-VEGF did not influence body mass in SOD1 mice.

RT-PCR for the AAV4-IGF-1 vector demonstrated that vector was present in the cortex, brainstem, and spinal cord following intraventricular delivery (FIG. 11B).

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

TABLE 1

Potential gene pairs for use in a recombinant viral vector

| Gene | IGF-1 | calbindin D28 | Parvalbumin | HIF1-alpha | SIRT-2 | CNTF |
|---|---|---|---|---|---|---|
| IGF-1 |  | X | X | X | X | X |
| calbindin D28 | X |  | X | X | X | X |
| parvalbumin | X | X |  | X | X | X |
| HIF1-alpha | X | X | X |  | X | X |
| SIRT-2 | X | X | X | X |  | X |
| VEGF | X | X | X | X | X | X |
| SMN-1 | X | X | X | X | X | X |
| SMN-2 | X | X | X | X | X | X |
| CNTF | X | X | X | X | X |  |
| shh | X | X | X | X | X | X |
| EPO | X | X | X | X | X | X |
| LOX | X | X | X | X | X | X |
| progranulin | X | X | X | X | X | X |
| prolactin | X | X | X | X | X | X |
| placenta lactogen | X | X | X | X | X | X |
| ghrelin | X | X | X | X | X | X |
| angiogenin | X | X | X | X | X | X |
| neuroserpin | X | X | X | X | X | X |

TABLE 2

Potential gene pairs for use in a recombinant viral vector

| Gene | progranulin | prolactin | placenta lactogen | ghrelin | angiogenin |
|---|---|---|---|---|---|
| IGF-1 | X | X | X | X | X |
| calbindin D28 | X | X | X | X | X |
| parvalbumin | X | X | X | X | X |
| HIF1-alpha | X | X | X | X | X |
| SIRT-2 | X | X | X | X | X |
| VEGF | X | X | X | X | X |
| SMN-1 | X | X | X | X | X |
| SMN-2 | X | X | X | X | X |
| CNTF | X | X | X | X | X |
| shh | X | X | X | X | X |
| EPO | X | X | X | X | X |
| LOX | X | X | X | X | X |
| progranulin |  | X | X | X | X |
| prolactin | X |  | X | X | X |
| placenta lactogen | X | X |  | X | X |
| ghrelin | X | X | X |  | X |
| angiogenin | X | X | X | X |  |
| neuroserpin | X | X | X | X | X |

TABLE 3

Potential gene pairs for use in a recombinant viral vector

| Gene | shh | EPO | LOX | VEGF | SMN-1 | SMN-2 | neuroserpin |
|---|---|---|---|---|---|---|---|
| IGF-1 | X | X | X | X | X | X | X |
| calbindin D28 | X | X | X | X | X | X | X |
| parvalbumin | X | X | X | X | X | X | X |
| HIF1-alpha | X | X | X | X | X | X | X |
| SIRT-2 | X | X | X | X | X | X | X |
| VEGF | X | X | X |  | X | X | X |
| SMN-1 | X | X | X | X |  | X | X |
| SMN-2 | X | X | X | X | X |  | X |
| CNTF | X | X | X | X | X | X | X |
| shh |  | X | X | X | X | X | X |
| EPO | X |  | X | X | X | X | X |
| LOX | X | X |  | X | X | X | X |
| progranulin | X | X | X | X | X | X | X |
| prolactin | X | X | X | X | X | X | X |
| placenta lactogen | X | X | X | X | X | X | X |
| ghrelin | X | X | X | X | X | X | X |
| angiogenin | X | X | X | X | X | X | X |
| neuroserpin | X | X | X | X | X | X |  |

REFERENCES

1. Leigh, P. N. & Swash, M. Cytoskeletal pathology in motor neuron diseases. *Adv Neurol* 56, 115-24 (1991).
2. Carpenter, S. Proximal axonal enlargement in motor neuron disease *Neurology* 18 841-51 (1968).
3. Gonatas, N. K. et al. Fragmentation of the Golgi apparatus of motor neurons in amyotrophic lateral sclerosis. *Am J Pathol* 140, 731-7 (1992).
4. Hirano, A. et al. Fine structural study of neurofibrillary changes in a family with amyotrophic lateral sclerosis. *J Neuropathol Exp Neurol* 43, 471-80 (1984).
5. Leigh, P. N. et al. Ubiquitin-immunoreactive intraneuronal inclusions in amyotrophic lateral sclerosis. Morphology, distribution, and specificity. *Brain* 114 (Pt 2), 775-88 (1991).
6. Delisle, M. B. & Carpenter, S, Neurofibrillary axonal swellings and amyotrophic lateral sclerosis. *J Neurol Sci* 63, 241-50 (1984).
7. Hirano, A. Neuropathology of ALS: an overview. *Neurology* 47, S63-6 (1996).
8. Rosen, D. R. et al. Mutations in Cu/Zn superoxide dismutase gene are associated with familial amyotrophic lateral sclerosis. *Nature* 362, 59-62 (1993).
9. Gurney, M. E. et al. Motor neuron degeneration in mice that express a human Cu,Zn superoxide dismutase mutation. *Science* 264, 1772-5 (1994).
10. Rowland, L. P. & Shneider, N. A. Amyotrophic lateral sclerosis. *N Engl J Med* 344, 1688-700 (2001).
11. Bruijn, L. I., Miller, T. M. & Cleveland, D. W. Unraveling the mechanisms involved in motor neuron degeneration in ALS. *Annu Rev Neurosci* 27, 723-49 (2004).
12. Cleveland, D. W. & Rothstein, J. D. From Charcot to Lou Gehrig: deciphering selective motor neuron death in ALS. *Nat Rev Neurosci* 2, 806-19 (2001).
13. Lindsay, R. M. Neurotrophic growth factors and neurodegenerative diseases: therapeutic potential of the neurotrophins and ciliary neurotrophic factor. *Neurobiol Aging* 15, 249-51 (1994).
14. Kaspar, B. K., Llado, J., Sherkat, N., Rothstein, J. D. & Gage, F. H. Retrograde viral delivery of IGF-1 prolongs survival in a mouse ALS model. *Science* 301, 839-42 (2003).
15. Clement, A. M. et al. Wild-type nonneuronal cells extend survival of SOD1 mutant motor neurons in ALS mice. *Science* 302, 113-7 (2003).
16. Matsushita, M. Projections from the lowest lumbar and sacral-caudal segments to the cerebellar nuclei in the rat, studied by anterograde axonal tracing. *J Comp Neurol* 404, 21-32 (1999).
17. Matsushita, M. & Gao, X. Projections from the thoracic cord to the cerebellar nuclei in the rat, studied by anterograde axonal tracing. *J Comp Neurol* 386, 409-21 (1997).
18. Matsushita, M. & Xiong, G. Projections from the cervical enlargement to the cerebellar nuclei in the rat, studied by anterograde axonal tracing. *J Comp Neurol* 377, 251-61 (1997).
19. Matsushita, M. & Yaginuma, H. Afferents to the cerebellar nuclei from the cervical enlargement in the rat, as demonstrated with the *Phaseolus vulgaris* leucoagglutinin method. *Neurosci Lett* 113, 253-9 (1990).
20. Matsushita, M. & Yaginuma, H. Projections from the central cervical nucleus to the cerebellar nuclei in the rat, studied by anterograde axonal tracing. *J Comp Neurol* 353, 234-46 (1995).
21. Voogd, J. The cerebellar nuclei and their efferent pathways. in *The rat nervous system* (ed. Paxinos, G.) 208-215 (Elsevier Academic Press, San Diego, 2004).
22. Dodge, J. C. et al. Gene transfer of human acid sphingomyelinase corrects neuropathology and motor deficits in a mouse model of Niemann-Pick type A disease. *Proc Natl Acad Sci USA* 102, 17822-7 (2005).
23. Corse, A. M. et al. Preclinical testing of neuroprotective neurotrophic factors in a model of chronic motor neuron degeneration. *Neurobiol Dis* 6, 335-46 (1999).
24. Seeburger, J. L. & Springer, J. E. Experimental rationale for the therapeutic use of neurotrophins in amyotrophic lateral sclerosis. *Exp Neurol* 124, 64-72 (1993).
25. Kasarskis, E. J. et al. A controlled trial of recombinant methionyl human BDNF in ALS: The BDNF Study Group (Phase III). *Neurology* 52, 1427-33 (1999).
26. Miller, R. G. et al. A placebo-controlled trial of recombinant human ciliary neurotrophic (rhCNTF) factor in amyotrophic lateral sclerosis. rhCNTF ALS Study Group. *Ann Neurol* 39, 256-60 (1996).
27. Borasio, G. D. et al. A placebo-controlled trial of insulin-like growth factor-I in amyotrophic lateral sclerosis. European ALS/IGF-I Study Group. *Neurology* 51, 583-6 (1998).
28. Lai, E. C. et al. Effect of recombinant human insulin-like growth factor-I on progression of ALS. A placebo-controlled study. The North America ALS/IGF-I Study Group. *Neurology* 49, 1621-30 (1997).
29. Gorio, A., Lesma, E., Madaschi, L. & Di Giulio, A. M. Co-administration of IGF-I and glycosaminoglycans greatly delays motor neurone disease and affects IGF-I expression in the wobbler mouse: a long-term study. *J Neurochem* 81, 194-202 (2002).
30. Hantai, D. et al. Beneficial effects of insulin-like growth factor-I on wobbler mouse motoneuron disease. *J Neurol Sci* 129 Suppl, 122-6 (1995).
31. Zheng, C., Nennesmo, I., Fadeel, B. & Henter, J. I. Vascular endothelial growth factor prolongs survival in a transgenic mouse model of ALS. *Ann Neurol* 56, 564-7 (2004).
32. Nagano, I. et al. Therapeutic benefit of intrathecal injection of insulin-like growth factor-1 in a mouse model of Amyotrophic Lateral Sclerosis. *J Neurol Sci* 235, 61-8 (2005).
33. Azzouz, M. et al. VEGF delivery with retrogradely transported lentivector prolongs survival in a mouse ALS model. *Nature* 429, 413-7 (2004).
34. Federici, T. & Boulis, N. M. Gene-based treatment of motor neuron diseases. *Muscle Nerve* 33, 302-23 (2006).
35. Boillee, S. & Cleveland, D. W. Gene therapy for ALS delivers. *Trends Neurosci* 27, 235-8 (2004).
36. Chirmule, N. et al. Immune responses to adenovirus and adeno-associated virus in humans. *Gene Ther* 6, 1574-83 (1999).
37. High, K. A. Clinical gene transfer studies for hemophilia B. *Semin Thromb Hemost* 30, 257-67 (2004).
38. Maheshri, N., Koerber, J. T., Kaspar, B. K. & Schaffer, D. V. Directed evolution of adeno-associated virus yields enhanced gene delivery vectors. *Nat Biotechnol* 24, 198-204 (2006).
39. Braunstein G D, Rasor J L, Engvall E, Wade M E. Inter-relationships of human chorionic gonadotropin, human placental lactogen, and pregnancy-specific beta 1-glyco-protein throughout normal human gestation. Am J Obstet. Gynecol. 1980 Dec. 15; 138(8):1205-13.
40. Confavreux C, Hutchinson M, Hours M M, Cortinovis-Tourniaire P, Moreau T. Rate of pregnancy-related relapse in multiple sclerosis. Pregnancy in Multiple Sclerosis Group. N Engl J. Med. 1998 Jul. 30; 339(5):285-91.
41. Carson M. J., Behringer R. R., Brinster R. L. and McMorris F. A. (1993) Insulin-like growth factor I increases brain growth and central nervous system myelination in transgenic mice. Neuron 10, 729-740.
42. Gensert J M, Goldman J E (1997) Endogenous progenitors remyelinate demyelinated axons in the adult CNS. Neuron 19:197-203.
43. Gregg C, Shikar V, Larsen P, Mak G, Chojnacki A, Yong V W, Weiss S. White matter plasticity and enhanced remyelination in the maternal CNS. J. Neurosci. 2007 Feb. 21; 27(8):1812-23.
44. Handwerger S, Freemark M. The roles of placental growth hormone and placental lactogen in the regulation of human fetal growth and development. J Pediatr Endocrinol Metab. 2000 April; 13(4):343-56.
45. Lesniak M A, Gorden P, Roth J. Reactivity of non-primate growth hormones and prolactins with human growth hormone receptors on cultured human lymphocytes. Clin Endocrinol Metab. 1977 May; 44(5):838-49.
46. Levison S W, Young G M, Goldman J E (1999) Cycling cells in the adult rat neocortex preferentially generate oligodendroglia. J Neurosci Res 57:435-446.
47. Menn B, Garcia-Verdugo J M, Yaschine C, Gonzalez-Perez O, Rowitch D, Alvarez-Buylla A (2006) Origin of oligodendrocytes in the subventricular zone of the adult brain. Neurosci 26:7907-7918.
48. Pelton E W, Grindeland R E, Young E, Bass N H. Effects of immunologically induced growth hormone deficiency on myelinogenesis in developing rat cerebrum. Neurology. March; 27(3):282-8.
49. Peters A, Sethares C (2004) Oligodendrocytes, their progenitors and other neuroglial cells in the aging primate cerebral cortex. Cereb Cortex 14:995-1007.
50. Polito A, Reynolds R (2005) NG2-expressing cells as oligodendrocyte progenitors in the normal and demyelinated adult central nervous system. J Anat 207:707-716.
51. Selenkow H A, Saxena B N, Dana C L. Measurement and pathophysiologic significance of human placental lactogen. In Pecile A, Finzi C (eds). The Feto-Placental Unit. Amersterdam, Excerpta Medica, 1969, p340.
52. van Walderveen M A, Tas M W, Barkhof F, Polman C H, Frequin S T, Hommes O R, Valk J (1994) Magnetic resonance evaluation of disease activity during pregnancy in multiple sclerosis. Neurology 44:327-329.
53. Voskuhl R R (2003) Hormone-based therapies in MS. Int MS J 10:60-66.
54. Zumkeller W. Current topic: the role of growth hormone and insulin-like growth factors for placental growth and development. Placenta. 2000 July-August; 21(5-6):451-67.

---

We claim:

1. A method to deliver a transgene product to the spinal cord in a subject having spinal muscular atrophy, comprising: administering via intracerebroventricular injection a recombinant adeno-associated virus (AAV) vector comprising said transgene to at least one ventricle of the brain, whereby said transgene is expressed and the expressed protein product is delivered to the spinal cord, wherein the transgene is survival motor neuron gene 1 (SMN-1).

2. The method of claim 1 wherein the AAV vector is AAV4.

3. The method of claim 1 wherein the AAV vector is administered by direct injection into a lateral ventricle of the brain.

4. The method of claim 1 wherein the AAV vector is administered by direct injection into the fourth ventricle of the brain.

5. The method of claim 1 wherein said vector encodes a further protein selected from the group consisting of insulin growth factor-1 (IGF-1), calbindin D28, parvalbumin, HIF1-alpha, SIRT-2, VEGF, SMN-2, CNTF (Ciliary neurotrophic factor), sonic hedgehog (shh), erythropoietin (EPO), lysyl oxidase (LOX), progranulin, prolactin, ghrelin, neuroserpin, angiogenin, and placenta lactogen.

6. The method of claim 1 wherein said subject is a mammal.

7. The method of claim 6, wherein said mammal is selected from the group consisting of a rodent, a murine, a simian, and a human.

8. The method of claim 1, wherein said subject is a human patient.

9. The method of claim 8, wherein said human patient underexpresses an effective amount of a protein selected from the group consisting of SMN-1 and SMN-2.

* * * * *

SEQUENCE LISTING

```
<160> NUMBER OF SEQ ID NOS: 4

<210> SEQ ID NO 1
<211> LENGTH: 153
<212> TYPE: PRT
<213> ORGANISM: Homo sapiens

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 2
<211> LENGTH: 195
<212> TYPE: PRT
<213> ORGANISM: Homo sapiens
```

<400> SEQUENCE: 2

Met Gly Lys Ile Ser Ser Leu Pro Thr Gln Leu Phe Lys Cys Cys Phe
1               5                   10                  15
Cys Asp Phe Leu Lys Val Lys Met His Thr Met Ser Ser Ser His Leu
            20                  25                  30
Phe Tyr Leu Ala Leu Cys Leu Leu Thr Phe Thr Ser Ser Ala Thr Ala
        35                  40                  45
Gly Pro Glu Thr Leu Cys Gly Ala Glu Leu Val Asp Ala Leu Gln Phe
    50                  55                  60
Val Cys Gly Asp Arg Gly Phe Tyr Phe Asn Lys Pro Thr Gly Tyr Gly
65                  70                  75                  80
Ser Ser Ser Arg Arg Ala Pro Gln Thr Gly Ile Val Asp Glu Cys Cys
                85                  90                  95
Phe Arg Ser Cys Asp Leu Arg Arg Leu Glu Met Tyr Cys Ala Pro Leu
            100                 105                 110
Lys Pro Ala Lys Ser Ala Arg Ser Val Arg Ala Gln Arg His Thr Asp
        115                 120                 125
Met Pro Lys Thr Gln Lys Tyr Gln Pro Pro Ser Thr Asn Lys Asn Thr
    130                 135                 140
Lys Ser Gln Arg Arg Lys Gly Trp Pro Lys Thr His Pro Gly Gly Glu
145                 150                 155                 160
Gln Lys Glu Gly Thr Glu Ala Ser Leu Gln Ile Arg Gly Lys Lys Lys
                165                 170                 175
Glu Gln Arg Arg Glu Ile Gly Ser Arg Asn Ala Glu Cys Arg Gly Lys
            180                 185                 190
Lys Gly Lys
        195

<210> SEQ ID NO 3
<211> LENGTH: 890
<212> TYPE: DNA
<213> ORGANISM: Artificial Sequence
<220> FEATURE:
<223> OTHER INFORMATION: gene sequence of IGF-1

<400> SEQUENCE: 3
tcactgtcac tgctaaattc agagcagatt agagcctgcg caatggaata aagtcctcaa     60
aattgaaatg tgacattgct ctcaacatct cccatctctc tggatttcct tttgcttcat    120
tattcctgct aaccaattca ttttcagact ttgtacttca gaagcaatgg gaaaaatcag    180
cagtcttcca acccaattat ttaagtgctg cttttgtgat tcttgaagg tgaagatgca    240
caccatgtcc tcctcgcatc tcttctacct ggcgctgtgc ctgctcacct tcaccagctc    300
tgccacggct ggaccggaga cgctctgcgg ggctgagctg gtggatgctc ttcagttcgt    360
gtgtggagac aggggctttt atttcaacaa gcccacaggg tatggctcca gcagtggcgc    420
ctcagacagg catcgtggat gagtgctgct tccgagctg tgatctaagg aggctcggag    480
ggagatgtat tgcgcacccc tcaagcctgc caagtcagct cgctctgtcc gtgcccagcg    540
ccacaccgac atgcccaaga cccagaagga agtacatttg aagaacgcaa gtagagggag    600
tgcaggaaac aagaactaca ggatgtagga agacctcct gaggagtgaa gagtgacatg    660
ccaccgcagg atcctttgct ctgcacgagt acctgttaa actttggaac acctaccaaa    720
aaataagttt gataacattt aaaagatggg cgtttccccc aatgaaatac acaagtaaac    780
attccaacat tgtctttagg agtgatttgc accttgcaaa aatggtcctg gagttggtag    840

```
aatgctgttg atcttttatc aataatgttc tatagaaaag aaaaaaaaat                890

<210> SEQ ID NO 4
<211> LENGTH: 11
<212> TYPE: PRT
<213> ORGANISM: Artificial Sequence
<220> FEATURE:
<223> OTHER INFORMATION: TAT transduction domain

<400> SEQUENCE: 4

Tyr Gly Arg Lys Lys Arg Arg Gln Arg Arg Arg
1               5                   10
```